United States Patent [19]

Takiguchi et al.

[11] Patent Number: 5,700,892

[45] Date of Patent: Dec. 23, 1997

[54] FILM-FORMING RESIN AND HAIR COSMETIC COMPOSITION CONTAINING THE SAME

[75] Inventors: Osamu Takiguchi; Naomi Hori; Takashi Oda, all of Wakayama, Japan

[73] Assignee: Kao Corporation, Tokyo, Japan

[21] Appl. No.: 805,248

[22] Filed: Feb. 24, 1997

[30] Foreign Application Priority Data

Mar. 12, 1996  [JP]  Japan .................. 8-054790

[51] Int. Cl.$^6$ .................. C08F 220/54; C08F 226/02; C08F 216/14; C08F 218/02

[52] U.S. Cl. .................. 526/306; 526/307.2; 526/307.3; 526/307.5; 526/307.7; 424/70.17

[58] Field of Search .................. 526/306, 307.2, 526/307.3, 307.5, 307.7; 424/70.17

[56] References Cited

U.S. PATENT DOCUMENTS 4,111,922  9/1978  Beede et al. .................. 526/292

*Primary Examiner*—Joseph L. Schofer
*Assistant Examiner*—Wu C. Cheng
*Attorney, Agent, or Firm*—Oblon, Spivak, McClelland, Maier & Neustadt, P.C.

[57] ABSTRACT

A film-forming resin which is a copolymer comprising (a) 30–80 mol % of a (meth)acrylamide monomer represented by the formula (1) wherein $R^1$ represents $CH_3$ or the like, $R^2$ and $R^3$ each represents H or a $C_4$–$C_{12}$ alkyl group; (b) 2–50 mol % of a (meth)acrylamide monomer represented by the formula (2) wherein $R^4$ and $R^5$ each represents H or a $C_1$–$C_3$ alkyl group; (c) 0.0001–50 mol % of a (meth)acrylate monomer or (meth)acrylamide monomer represented by the formula (3) wherein $R^6$ represents $C_2$–$C_3$ alkylene group, $R^7$,$R^8$ and $R^{10}$ each represents $CH_3$ or $C_2H_5$, $R^9$ represents an alkyl or phenyl group, a stands for 0 or 1 and b stands for 0 or 1, (d) 0–40 mol % of a (meth) acrylate monomer represented by the formula (4) wherein $R^{11}$ and $R^{12}$ each represents a $C_2$–$C_4$ alkylene group, $R^{13}$ represents H, $CH_3$ or $C_6H_5$ and d and e stands for an integer of 0–50; and (e) 0–20.0 mol % of a cross-linkable vinyl monomer; and a hair cosmetic composition containing the resin.

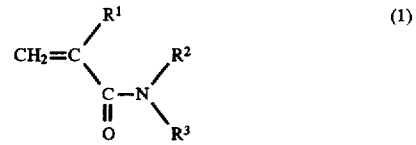

(1)

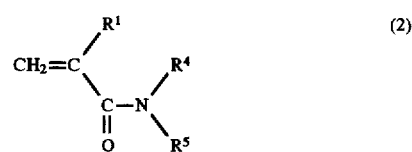

(2)

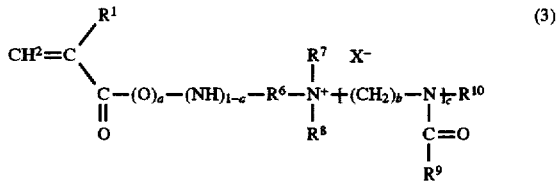

(3)

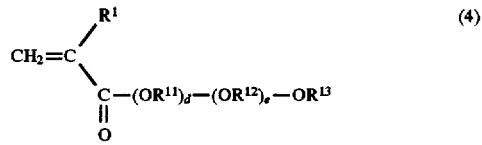

(4)

The film-forming resin according to the present invention permits the retention of hair style for long hours even under high humidity conditions and in addition, has excellent removability upon hair washing. It permits the retention of beautiful finish when used as a hair-styling resin.

4 Claims, No Drawings

FILM-FORMING RESIN AND HAIR COSMETIC COMPOSITION CONTAINING THE SAME

BACKGROUND OF THE INVENTION

1. Field of the Invention

The present invention relates to a film-forming resin and a hair cosmetic composition containing the resin.

2. Description of the Related Art

It is the common practice to add a film-forming resin to a hair cosmetic composition such as hair setting foam, hair setting lotion or the like in order to impart hair styling power or set retention to the composition. For the preparation of such a film-forming resin, polyvinyl pyrrolidone, a polyvinyl pyrrolidone-vinyl acetate copolymer, a vinyl acetate-crotonic acid copolymer or the like is used.

A film-forming resin to be added to a hair cosmetic composition is required to have properties such as long-time retention of hair style which has been set and easy removability by a shampoo or water upon hair washing.

The conventional polymer having good water solubility is however accompanied with the drawback that owing to high hygroscopicity under high humidity conditions, its stickiness is remarkable. It therefore does not satisfy both the requirements for stickiness-free finish under high humidity conditions and excellent removability upon hair washing at the same time. To meet such situations, the conventional film-forming resin is improved only in stickiness at the sacrifice of the improvement in the removability upon hair washing, or is added with a lubricant such as silicone oil to cover up the remarkable stickiness under high humidity conditions.

Furthermore, the conventional film-forming resin is accompanied with the problems that owing to moisture absorption, the film on the hair softens so that hair style which has been set cannot be retained sufficiently under high humidity conditions, and when the resin is used for a hair setting foam as a hair styling resin, the hair setting foam taken on hands forms a complex with the salt contained in the sweat or the like of hands and fingers and causes salting-out so that it does not bring about satisfactory effects.

The present inventors conducted an extensive research with a view toward overcoming the above-described problems and found a film-forming resin having excellent hair set retention even under high humidity conditions. They already filed a patent application on the resin (Japanese Patent Laid-Open No. 180911/1990). Even the film-forming resin however has a drawback that it becomes sticky owing to moisture absorption under high humidity conditions and it is necessary to improve the touch feeling by adding a special lubricant to the resin. Moreover, the film-forming resin has excellent water solubility but is accompanied with the drawback that a cationic unit which is a constituent of the resin forms a complex with an anionic surfactant so that it is sparingly insoluble in a shampoo solution.

SUMMARY OF THE INVENTION

An object of the present invention is therefore to provide a film-forming resin which is free from stickiness and permits retention of the hair style, which has been set, for long hours even under high humidity conditions; is excellent in removability upon hair washing so that the resin can be removed easily with a shampoo or water; and even if used for a hair setting foam as a hair styling resin, does not cause salting-out, has beautiful finish and is free from the release of the surface film by brushing or the like.

Under the forgoing in view, the present inventors have proceeded with an extensive research. As a result, it has been found that without losing the essential properties of the film-forming resin disclosed in Japanese Patent Laid-Open No. 180911/1990, it becomes possible to impart the resin with salting-out resistance and to overcome both problems, that is, stickiness under high humidity conditions and removability by a shampoo by using a low-molecular-weight (meth)acrylamide monomer and a poly-N-acylalkyleneimino-introduced (meth)acrylate monomer or (meth)acrylamide monomer instead of the (meth)acrylate monomer which is a constituent of the copolymer of the above application, leading to the completion of the present invention.

In one aspect of the present invention, there is thus provided a film-forming resin which is a copolymer composed of:

(a) 30 mol % to 80 mol % of a (meth)acrylamide monomer represented by the following formula (1):

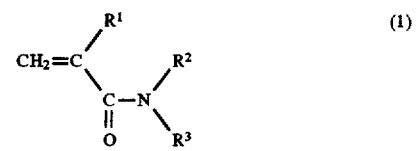

wherein $R^1$ represents a hydrogen atom or a methyl group, $R^2$ and $R^3$ are the same or different and each independently represents a hydrogen atom or a $C_{4-12}$ alkyl group with the proviso that $R^2$ and $R^3$ do not represent a hydrogen atom at the same time;

(b) 2 mol % to 50 mol % of a (meth)acrylamide monomer represented by the following formula (2):

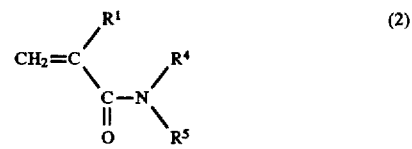

wherein $R^1$ has the same meaning as defined above and $R^4$ and $R^5$ are the same or different and each independently represents a hydrogen atom or a $C_{1-3}$ alkyl group;

(c) 0.0001 mol % to 50 mol % of a (meth)acrylate monomer or (meth)acrylamide monomer represented by the following formula (3):

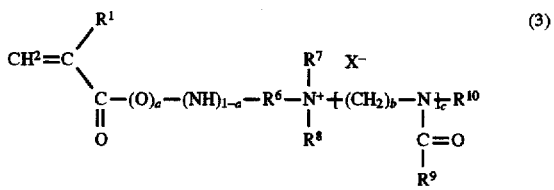

wherein $R^1$ has the same meaning as defined above, $R^6$ represents a $C_{2-3}$ alkylene group, $R^7$ and $R^8$ are the same or different and each independently represents a methyl or ethyl group, $R^9$s are the same or different and each independently represents a $C_{1-22}$ alkyl or phenyl group, $R^{10}$ represents a methyl or ethyl group, a stands for an integer of 0 or 1, b represents an integer of 2 or 3, c represents an integer of 2–10,000 and $X^-$ represents a counterion of a quaternary ammonium salt;

(d) 0 mol % to 40 mol % of a (meth)acrylate monomer represented by the following formula (4):

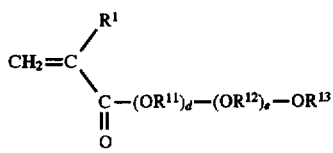

(4)

wherein $R^1$ has the same meaning as defined above, $R^{11}$ and $R^{12}$ are the same or different and each independently represents a $C_{2-4}$ alkylene group, $R^{13}$ represents a hydrogen atom, a $C_{1-10}$ alkyl group or a phenyl group, d and e each independently represents an integer of 0–50 with the proviso that they do not stand for 0 at the same time; and (e) 0 mol % to 20.0 mol % of a cross-linkable vinyl monomer.

In another aspect of the present invention, there is also provided a hair cosmetic composition comprising the above-described film-forming resin.

The film-forming resin according to the present invention has very low stickiness under the high humidity conditions as well as normal humidity conditions and has excellent hair styling power and set retention, while it can be easily washed away by ordinary washing with water or shampoo because of having a quaternized amino group. In addition, the film-forming resin according to the present invention has high compatibility with LPG. The film-forming resin shows good compatibility not only with a hydrocarbon solvent such as LPG but also an organic solvent such as aromatic, halogen, ketone or ester type solvent so that it can be used in various forms. For example, it can also be used as a surface treating agent for natural leather, synthetic leather, rubber, plastics or glass. It can impart various base materials with good touch feeling, luster or gloss. Depending on the composition, it can give them even antiseptic effects, antistatic effects or the like. It also shows good adhesion to the protein such as nail or skin so that it can be used for manicure.

DETAILED DESCRIPTION OF THE PREFERRED EMBODIMENTS

Examples of the (meth)acrylamide monomer represented by the formula (1) which is used for the preparation of the film-forming resin of the present invention include N-n-butyl (meth)acrylamide, N-tert-butyl (meth)acrylamide, N-octyl (meth)acrylamide, N-lauryl (meth)acrylamide, N-1-methylundecyl (meth)acrylamide, N-2-ethylhexyl (meth) acryl-amide and N-tert-octyl (meth)acrylamide. Among them, N-branched alkyl (meth)acrylamide such as N-tert-butyl (meth)acrylamide, N-tert-octyl (meth)acrylamide and N-2-ethylhexyl (meth) acrylamide are particularly preferred.

They may be used either singly or in combination. The using amount is 30–80 mol %, preferably 40–70 mol % based on the total amount of the monomers.

Examples of the (meth)acrylamide monomer (2) represented by the formula (2) include (meth)acrylamide, N-methyl (meth)acrylamide, N-ethyl (meth)acrylamide, N-isopropyl (meth)acrylamide, N,N-dimethyl (meth) acrylamide and N,N-diethyl (meth)acrylamide. Among them, N-methyl (meth)acrylamide, N-ethyl (meth) acrylamide, N,N-dimethyl (meth)acrylamide and N,N-diethyl (meth)acrylamide are particularly preferred.

They may be used either singly or in combination. The using amount is 2–50 mol %, preferably 10–35 mol %, based on the total amount of the monomers.

The (meth)acrylate monomer or (meth)acrylamide monomer represented by the formula (3) is prepared by reacting the tertiary amino group of a (meth)acrylamide monomer represented by the following formula (5):

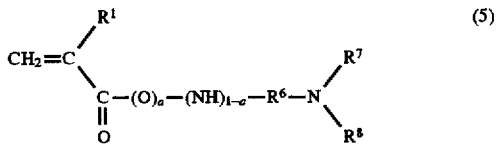

(5)

wherein $R^1$ has the same meaning as defined above, $R^6$ represents a $C_{2-3}$ alkylene group, and $R^7$ and $R^8$ are the same or different and each independently represents a methyl or ethyl group, with a terminal-reactive poly(N-acylalkylene imine) produced by the ring-opening polymerization of a cyclic iminoether represented by the following formula (6):

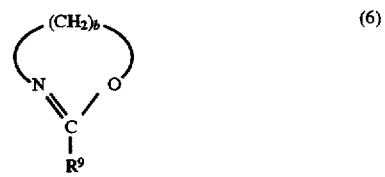

(6)

wherein b stands for an integer of 2 or 3 and $R^9$ has the same meaning as defined above, in the presence of $(R^{10})_2SO_4$ . . . (7) in which $R^{10}$ has the same meaning as defined above. The reaction of the tertiary amino group of a (meth) acrylamide monomer represented by the formula (5) with the terminal-reactive poly(N-acylalkylene imine) however may be carried out after obtaining a tertiary-amino-containing polymer by copolymerizing the monomers (1), (2), (4) and (5) or copolymerizing the monomers represented by the formula (1), (2), (4) and (5) and the cross-linkable monomer.

Examples of the (meth) acrylate or (meth)acrylamide monomer represented by the formula (5) include N,N-dimethylaminoethyl (meth)acrylate, N,N-diethylaminoethyl (meth)acrylate, N,N-dimethylaminopropyl (meth)acrylate, N,N-dimethylaminopropyl (meth)acrylamide and N,N-diethylaminopropyl (meth)acrylamide.

They may be used either singly or in combination. The using amount is 0.0001–50 mol %, preferably 0.01–10 mol %, more preferably 0.1–1 mol %, based on the total amount of the monomers.

Examples of the cyclic iminoether represented by the formula (6) include 2-substituted-2-oxazoline and 2-substituted-2-oxazine. It is preferred that the molecular weight of a poly(n-acylalkylene imine) falls within a range of from 200 to 100,000.

$R^9$s are the same or different and each independently represents a saturated alkyl group having 1–22 carbon atoms and a phenyl group, with methyl, ethyl, n-propyl and iso-propyl groups being particularly preferred.

And, c stands for an integer of 2–10,000, with 50–200 being preferred.

The monomer represented by the formula (4) is a (meth) acrylate having a polyoxyalkylene chain. In the formula, $R^{11}$ represents a hydrogen atom, a $C_{1-10}$ alkyl group or a phenyl group. Among them, a hydrogen atom and a $C_{1-4}$ alkyl group are preferred, with a methyl group being particularly preferred. Examples of such a (meth) acrylate monomer (4) include hydroxyethyl (meth)acrylate, hydroxypropyl (meth) acrylate, polyethylene glycol mono(meth)acrylate, polypropylene glycol mono(meth)acrylate, methoxypolyethylene glycol mono(meth)acrylate, methoxypolypropylene glycol mono(meth) acrylate, ethoxypolyethylene glycol mono (meth) acrylate, butoxypolyethylene glycol mono(meth) acrylate and phenoxypolyethylene glycol mono(meth) acrylate.

The polyoxyalkylene chain is a homopolymer or copolymer of a $C_{2-4}$ alkylene oxide. In the case of a copolymer, the polyoxyalkylene chain may either be a block copolymer or a random copolymer of ethylene oxide, propylene oxide or the like.

The polymerization degree of an alkylene oxide can be analyzed by gas chromatography and an alkylene oxide having the polymerization degree of 1–50 on average is preferred.

These monomers may be used either singly or in combination. The using amount is 0–40 mol %, preferably 0–20 mol %, more preferably 0–5 mol %, each based on the total amount of monomers.

The cross-linkable vinyl monomer (e) is a compound containing at least two carbon-carbon unsaturated double bonds per molecule and has a property of crosslinking with another monomer.

Representative examples of the cross-linkable vinyl monomer include (meth)acrylic monomers containing at least two carbon-carbon unsaturated double bonds per molecule such as ethylene glycol di(meth)acrylate, polyoxyethylene di(meth)acrylate, trimethylolpropane tri(meth)acrylate, pentaerythritol tri(meth) acrylate and polypropylene glycol di(meth)acrylate; and (meth)acrylamide monomers containing at least two carbon-carbon unsaturated double bonds per molecule such as methylenebis (meth)acrylamide, 1,2-bis (meth)acrylamide ethane and 1,5-bis(meth)allyl amide pentane, however, the present invention is not limited to such examples. Incidentally, in the present invention, the cross-linkable vinyl monomers can be used either singly or in combination.

In the case where the cross-linkable vinyl monomer (e) is suitably used for the application having a high viscosity, for example, a hair gel, the using amount is 0.1–20.0 mol %, preferably 1.0–10.0 mole %, each based on the total amount of the monomers. On the other hand, in the case where it is suitably used for the application having a low viscosity, for example, an aerosol composition or hair setting foam, the using amount is 0–10.0 mol %, preferably 0–5.0 mol %, each based on the total amount of the monomers.

The film-forming resin of the present invention can be prepared by using the monomers represented by (1), (2), (4) and (5) in combination or using the monomers represented by (1), (2), (4) and (5) and the cross-linkable monomer in combination; copolymerizing the resulting monomer mixture by the known polymerization method in the presence of a radical polymerization initiator; and then reacting the tertiary amino group of the resulting polymer with a terminal-reactive poly(N-acylalkylene imine). Alternatively, it can be prepared by reacting the tertiary amino group of the (meth)acrylamide monomer represented by the formula (5) with a terminal-reactive poly(N-acyl-alkylene imine) to prepare a (meth)acrylamide monomer represented by the formula (3); using the resulting monomer and the monomers represented by the formulas (1), (2) and (4) in combination or using the resulting monomer, the monomers represented by the formulas (1), (2) and (4) and the cross-linkable monomer in combination; and then copolymerizing the resulting mixture by the known polymerization method in the presence of a radical polymerization agent.

Examples of the known polymerization method usable for the preparation of the film-forming resin of the present invention include bulk polymerization, solution polymerization, suspension polymerization and emulsion polymerization. Among them, solution polymerization is preferred. As a solvent used in the solution polymerization, a water-miscible organic solvent (a mixture with water is possible) is preferred. The organic solvent can be used either singly or as a mixture of at least two components. Examples of such a water-miscible organic solvent include $C_{1-3}$ aliphatic alcohols such as methanol, ethanol or propanol; ketones such as acetone or methyl ethyl ketone; ethers such as tetrahydrofuran, glyme, diglyme or dioxane; and esters such as methyl acetate or ethyl acetate. Among them, methanol, ethanol, and acetone, and a mixture thereof with water are preferred.

Preferred examples of the radical polymerization initiator usable in the present invention include azo compounds such as 2,2'-azobisisobutylonitrile, 2,2'-azobis (2,4-dimethylvaleronitrile), 2,2'-azobis(4-methoxy-2,4-dimethylvaleronitrile), dimethyl-2,2'-azobis isobutylate, 2,2'-azobis(2-methylbutylonitrile) and 1,1'-azobis (1-cyclohexanecarbonitrile). In addition, organic peroxides such as tert-butyl peroctoate, dicumyl peroxide, di-tert-butyl peroxide and dibenzoyl peroxide can also be used. The use of the organic peroxide as a polymerization initiator is however not industrially preferred, because there is a possibility of the organic peroxide causing a redox reaction with the tertiary amino group of the monomer (3) so that the reaction cannot be controlled easily, for example, the polymerization should be carried out at a low temperature not higher than 40° C.

It is preferred to use the polymerization initiator in an amount of 0.001–10.0 mol %, more preferably 0.01–5.0 mol % based on the amount of the monomer mixture.

The polymerization may be carried out by charging the whole amounts of the monomer mixture and the polymerization initiator, followed by heating, or by the dropwise addition or charging in portions of each monomer and/or the polymerization initiator.

The polymerization temperature is selected as needed depending on the kinds of the radical polymerization initiator, the monomer and the solvent to be employed, but is generally 30°–100° C., with 40°–90° C. being preferred. The copolymerization can be conducted in the atmosphere of an inert gas such as nitrogen, as is always conducted.

After the polymerization step, the copolymer can be isolated from the polymerization reaction mixture by the known method such as reprecipitation or solvent removal. Alternatively, unreacted monomers can be removed from the resulting copolymer by the known method such as repetition of re-precipitation, membrane separation, chromatography, extraction, or the like.

The molecular weight [in terms of polyethylene glycol, as measured by gel permeation chromatography] of the copolymer so obtained can be controlled to 1,000–1,000,000 under the selected polymerization conditions. In the present invention, the copolymer having a molecular weight of 10,000–500,000 is preferred.

Examples of the hair cosmetic composition containing the film-forming resin according to the present invention include hair setting foam, hair spray, setting lotion, gel, shampoo and rinse. It can be used as various forms such as aqueous solution, aqueous alcoholic solution, emulsion, cream and gel. Among them, the hair cosmetic composition for setting hair style is preferred. The above-exemplified hair cosmetic compositions can be classified roughly into those using a propellant such as hair setting foam or hair spray and those without using a propellant such as setting lotion, hair setting gel, shampoo or rinse. In the present invention, the hair cosmetic composition using a propellant is preferred.

In the case of the hair cosmetic composition using a propellant, it is preferred to incorporate, in the stock solution, 0.01–15 wt. %, preferably 2–8 wt. %, of the film-forming resin of the present invention, 50–99.8 wt. % of a solvent selected from lower alcohols such as ethanol, polyols or water, and 0.1–20 wt. % of a lubricant selected from hydrocarbons, ester oils, silicone and its derivatives or natural fats and oils. In addition, it is preferred to use as needed 0.5–3.0 wt. % of a touch feel improver—such as higher alcohol, octyldodecyl myristate, glycerin, polyethylene glycol or polyoxyethylene hexadecyl ether—which is in the form of a transparent liquid or transparent 1.5 paste at 50° C. and is in the form of a solid or white wax at 25° C.; and 0.1–3.0 wt. % of a film forming assistant such as alkylene-oxide-added type alkyl ether, e.g., polyoxyethylene stearyl ether, or cationic high molecules, e.g., cationized cellulose.

Examples of the propellant include 100 wt. % of LPG, 100 wt. % of dimethyl ether (DME), 100 wt. % of flon gas, LPG/flon mixed gas and LPG/DME mixed gas. In particular, a propellant composed of 50–100 wt. % of LPG gas is suitably employed. It is preferred that the weight ratio of the stock solution to the propellant in the spray-type hair cosmetic composition is 5:95–70:30, with 20:80 to 50:50 being particularly preferred.

In the gel form such as hair setting gel, it is preferred to use 0.5–10.0 wt. %, preferably 1.0–3.0 wt. %, of the film-forming resin of the present invention, 0.5–2.0 wt. % of a viscosity modifier composed of a water-soluble high molecule such as polyacrylic acid or hydroxyethyl cellulose, and a solvent composed of purified water and optionally a lower alcohol.

The film-forming resin of the present can also be used for shampoo, rinse or the like and in this case, it is preferred to use it in an amount of 0.1–5.0 wt. %, preferably 0.5–2.0 wt. %.

In such a hair cosmetic composition, a generally-used pharmaceutically-effective agent, such as antiseptic, ultraviolet absorber, sequestering agent or dandruff preventive and also a colorant, perfume or the like may be added according to the using purpose.

The present invention will hereinafter be described in more detail by synthesis examples and examples. It should however be borne in mind that the present invention is not limited to or by the following examples.

SYNTHESIS EXAMPLES 1-7

In each of Synthesis Examples 1-7, in a four-necked flask equipped with a reflux condenser, dropping funnel, thermometer, nitrogen gas inlet tube and stirrer, 100 parts by weight of ethanol were charged and heated to 60° C. To the resulting mixture, a monomer solution composed of 100 parts by weight of a monomer mixture having a composition as shown in Table 1 and 200 parts by weight of ethanol (addition of water as needed) and an initiator solution obtained by dissolving an initiator in 33 parts by weight of ethanol were added dropwise over 1.5 hours under the nitrogen gas atmosphere. They were kept at 60° C. for 8 hours to cause reaction. After polymerization, a solution of the polymer in ethanol was poured in n-hexane to carry out purification by reprecipitation, followed by vacuum drying at 20 mmHg and 60° C. for 12 hours.

The polymers so obtained were all in the form of a white solid. The weight-average molecular weight [in terms of GPC: polyethylene glycol (PEG) in a dimethylformamide (DMF) solution] of Synthesis Example 1 was 118,900 and those of Synthesis Examples 2-12 fell within a range of 70,000 to 500,000.

TABLE 1

| | | | Synthesis Ex. | | | | | | |
|---|---|---|---|---|---|---|---|---|---|
| | | | 1 | 2 | 3 | 4 | 5 | 6 | 7 |
| Monomer (mol %) | (1) | N-t-butyl acrylamide | 65 | 60 | 60 | 55 | | 50 | 55 |
| | | N-t-octyl acrylamide | | | | | 55 | | |
| | (2) | N,N-dimethyl acrylamide | 30 | 30 | 39.5 | | 39.5 | 30 | 25 |
| | | N,N-diethyl acrylamide | | | | 30 | | | |
| | (4) | Methoxypolyethylene glycol methacrylate*[1] | 3.5 | 5 | | | 1.5 | 17 | |
| | | 2-Hydroxyethyl methacrylate | | | | 10 | | | 15 |
| | (5) | N,N-dimethyl aminoethyl acrylate | | | | | | 3 | |
| | | N,N-dimethylaminopropyl acrylamide | 1 | 5 | 0.5 | 5 | 0.5 | | 5 |
| Cross-linkable monomer*[2] | | | 0.5 | | | | 0.5 | | |
| Initiator (mol %) | 2,2'-Azobi-(2,4-dimethyl valeronitrile) | | 0.2 | 0.2 | 0.2 | 0.2 | | 0.2 | |
| | Azobis isobutylonitrile | | | | | | | 0.3 | 0.2 |

*[1]: Polyethylene glycol having a molecular weight of 400
*[2]: Tripropylene glycol dimethacrylate

SYNTHESIS EXAMPLE 8-10

In 60 g of dehydrated ethyl acetate, diethyl sulfate and 2-ethyl-2-oxazoline were dissolved, each in an amount as shown in Table 2, followed by heating under reflux for 5 hours under the nitrogen atmosphere, whereby a terminal-reactive poly(N-propionylethylene imine) was synthesized.

TABLE 2

| | 8 | 9 | 10 |
|---|---|---|---|
| Diethyl sulfate*[1] | 3.56 (0.023) | 0.757 (0.0049) | 0.384 (0.0025) |
| 2-Ethyl-2-oxazoline*[1] | 27.5 (0.277) | 29.2 (0.294) | 29.6 (0.298) |
| Molecular weight predetermined | 1200 | 5900 | 12000 |

*[1]: Unit g(mol)

SYNTHESIS EXAMPLES 11–25

In each of Synthesis Examples 11–25, the reaction between a copolymer and a terminal-reactive poly(N-propionyl ethyleneimine) was conducted according to the combination shown in Table 3. In a four-necked flask equipped with a reflux condenser, dropping funnel, thermometer, nitrogen gas inlet tube and stirrer, 50 parts by weight of dehydrated ethyl acetate and 50 parts by weight of the polymer obtained in one of Synthesis Example 1–7 were charged, followed by heating to 70° C. One of the terminal-reactive poly(N-propionylethylene imine) which had been obtained in Synthesis Example 8–10 was thereafter added to the above polymer such that the molar number of the tertiary amino group contained in the polymer obtained in one of Synthesis Examples 1–7 is equal to the molar number of the terminal-reactive poly(N-propionylethyleneimine). They were heated under reflux for 12 hours under the nitrogen gas atmosphere. The reaction mixture was concentrated under reduced pressure. From the concentrate, ethyl acetate was removed by drying, whereby the target polymer was obtained.

TABLE 3

| | Synthesis Ex. | | | | |
|---|---|---|---|---|---|
| | 11 | 12 | 13 | 14 | 15 |
| Copolymer | Synthesis Ex. 1 | Synthesis Ex. 1 | Synthesis Ex. 1 | Synthesis Ex. 2 | Synthesis Ex. 2 |
| Terminal-reactive poly(N-propionyl-ethylene imine) | Synthesis Ex. 8 | Synthesis Ex. 9 | Synthesis Ex. 10 | Synthesis Ex. 9 | Synthesis Ex. 10 |

| | Synthesis Ex. | | | | |
|---|---|---|---|---|---|
| | 16 | 17 | 18 | 19 | 20 |
| Copolymer | Synthesis Ex. 3 | Synthesis Ex. 3 | Synthesis Ex. 3 | Synthesis Ex. 4 | Synthesis Ex. 4 |
| Terminal-reactive poly(N-propionyl-ethylene imine) | Synthesis Ex. 8 | Synthesis Ex. 9 | Synthesis Ex. 10 | Synthesis Ex. 8 | Synthesis Ex. 9 |

| | Synthesis Ex. | | | | |
|---|---|---|---|---|---|
| | 21 | 22 | 23 | 24 | 25 |
| Copolymer | Synthesis Ex. 5 | Synthesis Ex. 5 | Synthesis Ex. 6 | Synthesis Ex. 7 | Synthesis Ex. 7 |
| Terminal-reactive poly(N-propionyl-ethylene imine) | Synthesis Ex. 9 | Synthesis Ex. 10 | Synthesis Ex. 10 | Synthesis Ex. 8 | Synthesis Ex. 9 |

EXAMPLES 1–15

In each of Examples 1–15, the components as shown in the following table were mixed, whereby hair setting foam was obtained.

TABLE 4 (1)

(wt. %)

| | | Examples | | | | | | | |
|---|---|---|---|---|---|---|---|---|---|
| | Component | 1 | 2 | 3 | 4 | 5 | 6 | 7 | 8 |
| Stock Soln. | Copolymer of Synthesis Ex. 11 | 3.0 | | | | | | | |
| | Copolymer of Synthesis Ex. 12 | | 3.0 | | | | | | |
| | Copolymer of Synthesis Ex. 13 | | | 3.0 | | | | | |
| | Copolymer of Synthesis Ex. 14 | | | | 3.0 | | | | |
| | Copolymer of Synthesis Ex. 15 | | | | | 3.0 | | | |
| | Copolymer of Synthesis Ex. 16 | | | | | | 3.0 | | |
| | Copolymer of Synthesis Ex. 17 | | | | | | | 3.0 | |
| | Copolymer of Synthesis Ex. 18 | | | | | | | | 3.0 |
| | Copolymer of Synthesis Ex. 19 | | | | | | | | |
| | Copolymer of Synthesis Ex. 20 | | | | | | | | |
| | Copolymer of Synthesis Ex. 21 | | | | | | | | |
| | Copolymer of Synthesis Ex. 22 | | | | | | | | |
| | Copolymer of Synthesis Ex. 23 | | | | | | | | |
| | Copolymer of Synthesis Ex. 24 | | | | | | | | |
| | Copolymer of Synthesis Ex. 25 | | | | | | | | |

TABLE 4 (2)

(wt. %)

| | | Examples | | | | | | | |
|---|---|---|---|---|---|---|---|---|---|
| | Component | 1 | 2 | 3 | 4 | 5 | 6 | 7 | 8 |
| Stock Soln. | Polyoxyethylene lauryl ether ("Emulgen 109P", | 0.5 | 0.5 | 0.5 | 0.5 | 0.5 | 0.5 | 0.5 | 0.5 |

TABLE 4 (2)-continued (wt. %)

| Component | Examples | | | | | | | |
|---|---|---|---|---|---|---|---|---|
| | 1 | 2 | 3 | 4 | 5 | 6 | 7 | 8 |
| trade name; product of Kao Corporation) | | | | | | | | |
| Polyether-modified silicone ("KF-352A"; product of Shinetsu Chemical Industries Co.) | 1.5 | 1.5 | 1.5 | 1.5 | 1.5 | 1.5 | 1.5 | 1.5 |
| Ethanol | 10.0 | 10.0 | 10.0 | 10.0 | 10.0 | 10.0 | 10.0 | 10.0 |
| Purified water | | | | Balance | | | | |
| Perfume | 0.2 | 0.2 | 0.2 | 0.2 | 0.2 | 0.2 | 0.2 | 0.2 |
| Total | 100.0 | 100.0 | 100.0 | 100.0 | 100.0 | 100.0 | 100.0 | 100.0 |
| Propellant* | | | | LPG | | | | |

*Propellant: 100 wt. % of LPG, a stock solution:propellant weight ratio = 90:100

TABLE 5 (1)

(wt. %)

| | Component | Examples | | | | | | |
|---|---|---|---|---|---|---|---|---|
| | | 9 | 10 | 11 | 12 | 13 | 14 | 15 |
| Stock Soln. | Copolymer of Synthesis Ex. 11 | | | | | | | |
| | Copolymer of Synthesis Ex. 12 | | | | | | | |
| | Copolymer of Synthesis Ex. 13 | | | | | | | |
| | Copolymer of Synthesis Ex. 14 | | | | | | | |
| | Copolymer of Synthesis Ex. 15 | | | | | | | |
| | Copolymer of Synthesis Ex. 16 | | | | | | | |
| | Copolymer of Synthesis Ex. 17 | | | | | | | |
| | Copolymer of Synthesis Ex. 18 | | | | | | | |
| | Copolymer of Synthesis Ex. 19 | 3.0 | | | | | | |
| | Copolymer of Synthesis Ex. 20 | | 3.0 | | | | | |
| | Copolymer of Synthesis Ex. 21 | | | 3.0 | | | | |
| | Copolymer of Synthesis Ex. 22 | | | | 3.0 | | | |
| | Copolymer of Synthesis Ex. 23 | | | | | 3.0 | | |
| | Copolymer of Synthesis Ex. 24 | | | | | | 3.0 | |
| | Copolymer of Synthesis Ex. 25 | | | | | | | 3.0 |

TABLE 5 (2)

(wt. %)

| | Component | Examples | | | | | | |
|---|---|---|---|---|---|---|---|---|
| | | 9 | 10 | 11 | 12 | 13 | 14 | 15 |
| Stock Soln. | Polyoxyethylene lauryl ether ("Emulgen 109P", trade name; product of Kao Corporation) | 0.5 | 0.5 | 0.5 | 0.5 | 0.5 | 0.5 | 0.5 |
| | Polyether-modified silicone ("KF-352A"; product of Shinetsu Chemical Industries Co.) | 1.5 | 1.5 | 1.5 | 1.5 | 1.5 | 1.5 | 1.5 |
| | Ethanol | 10.0 | 10.0 | 10.0 | 10.0 | 10.0 | 10.0 | 10.0 |
| | Purified water | | | | Balance | | | |
| | Perfume | 0.2 | 0.2 | 0.2 | 0.2 | 0.2 | 0.2 | 0.2 |
| | Total | 100.0 | 100.0 | 100.0 | 100.0 | 100.0 | 100.0 | 100.0 |
| | Propellant* | | | | LPG | | | |

*Propellant: 100 wt. % of LPG, a stock solution:propellant weight ratio = 90:100

EXAMPLE 16

The following components were mixed, whereby a hair setting lotion was prepared.

| Components | (wt. %) |
| --- | --- |
| Copolymer of Synthesis Example 16 | 2.0 |
| Polyether-modified silicone ("KF-352A", trade name; product of Shin-etsu Chemicals Co., Ltd.) | 1.0 |
| Ethanol | 86.5 |
| Purified water | 10.0 |
| Perfume | 0.5 |
| Total | 100.0 |

EXAMPLE 17

The following components were mixed, whereby a hair shampoo was prepared.

| Components | (wt. %) |
| --- | --- |
| Lauryl polyoxyethylene sulfate triethanolamine salt (40 wt. % aqueous soln.) ("Emanol 20C", trade name; product of Kao Corporation) | 32.0 |
| Lauroyl diethanolamine | 4.0 |
| Polyethylene glycol ("PEG 6000", trade name; product of Sanyo Chemical Industries, Ltd.) | 1.0 |
| Copolymer of Synthesis Example 18 | 1.0 |
| Purified water | 61.5 |
| Perfume | 0.5 |
| Total | 100.0 |

EXAMPLE 18

The following components were mixed, whereby a hair gel was prepared.

| Components | (wt. %) |
| --- | --- |
| The copolymer of Synthesis Ex. 11 | 5.0 |
| Purified water | 77.0 |
| "Carbopol 940" (trade name; product of B. F. Goodrich) | 0.5 |
| Triethanolamine | 0.5 |
| Ethanol | 16.8 |
| Perfume | 0.2 |
| Total | 100.0 |

EXAMPLE 19

The following components were mixed, whereby an aerosol composition was prepared.

| Components | (wt. %) |
| --- | --- |
| Copolymer of Synthesis Example 16 | 2.5 |
| Dimethyl polysiloxane | 0.3 |
| Perfume | 0.15 |
| Anhydrous ethanol | 47.05 |
| LPG | 50.00 |
| Total | 100.0 |

EXAMPLE 20

The following components were mixed, whereby a hair rinse was prepared.

| Components | (wt. %) |
| --- | --- |
| Copolymer of Synthesis Example 18 | 1.0 |
| Stearyltrimethyl ammonium chloride | 2.0 |
| Cetyl alcohol | 2.0 |
| Purified water | 94.8 |
| Perfume | 0.2 |
| Total | 100.0 |

COMPARATIVE EXAMPLES 1–4

In a similar manner to Example 1 except that, in Comparative Examples 1–3, the copolymers (neutralized with 100% lactic acid) obtained in Synthesis Examples 1–3 of Japanese Patent Laid-Open No. 180911/1990 (incidentally, the monomer composition ratio of those copolymers are shown in Table 6) and in Comparative Example 4, a commercially-available copolymer of methyl vinyl ether and monobutyl maleate ("Gantretz ES425", trade name; product of ISP) were used, respectively, instead of the copolymer of Synthesis Example 1, whereby hair setting foams were prepared.

TABLE 6

| | | (wt. %) | |
| --- | --- | --- | --- |
| | Comp. Ex. 1 | Comp. Ex. 2 | Comp. Ex. 3 |
| (1) N-tert-butyl acrylamide | 55 | 65 | 55 |
| (2) Ethyl acrylate | 25 | | 25 |
| Methyl acrylate | | 15 | |
| (3) N,N-dimethylaminoethyl acrylate | 10 | 10 | |
| N,N-diethylaminoethyl methacrylate | | | 10 |
| (4) Methoxypolyethylene glycol (PEG400) methacrylate | 10 | 10 | 10 |
| Weight-average molecular weight | 104,300 | 135,600 | 118,400 |

EXAMPLE 21

The performance of each of the hair setting foams obtained in Examples 1–15 and Comparative Examples 1–4 and also that of the film-forming resin contained in it were evaluated as follows:

(1) Test on set retention

A bundle of hairs having a length of 18 cm and a weight of 1.5 g was moistened with water and wound round a rod, followed by natural drying. The rod was then removed from the curled bundle. The bundle so curled was coated with each of the setting foams obtained in Examples 1–15 and Comparative Examples 1–4, each in the same amount and was naturally dried. The dried and curled hair bundle was then hung in an air-conditioned box (20° C., 98% RH) and the loosening state of the curl was observed, whereby set retention was judged. The judgment was carried out by measuring the vertical length of the curled bundle under the hanging condition, and determining the relative length (%) of the hair bundle 30 minutes after hanging was started supposing that the set retention just after hanging was 100% and the set retention of the original uncurled length (18 cm) was 0%. The results are shown in Tables 7 and 8.

B: Good

C: Fair

D: Bad (5) Test on removability upon hair washing

In a similar manner and according to similar standards to those for the water solubility test in (4) except that the immersion in water was changed to immersion in water containing 3 wt. % of shampoo, the removability by a shampoo was evaluated.

TABLE 7

|  | Example | | | | | | | | | | | | | | |
| --- | --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 | 14 | 15 |
| Set retention | A | A | A | A | A | A | A | A | A | A | A | A | A | A | A |
| Stickiness | A | A | A | A | A | A | A | A | B | B | A | A | B | A | A |
| Stiffness | B | A | A | A | A | B | A | A | B | A | A | A | A | B | A |
| Luster | A | A | A | A | A | A | A | A | A | A | A | A | A | A | A |
| Water solubility | A | A | A | A | A | A | A | A | A | A | A | A | A | A | A |
| Removability | A | A | A | A | A | A | A | A | A | A | A | A | A | A | A |

| Evaluation standards of "set retention" | |
| --- | --- |
| Rank | State |
| A: | set retention of 81% or more. |
| B: | set retention of from 61% to 80%. |
| C: | set retention of from 51% to 60%. |
| D: | set retention of from 0% to 50%. |

(2) Organoleptic evaluation on stickiness and stiffness

To the human head model (wig) for experiment, each hair setting foam was sprayed and stiffness and stickiness were evaluated in accordance with the following standards. The results are shown in Tables 7 and 8.

Evaluation standards of "stiffness and stickiness"

A: Very good

B: Good

C: Fair

D: Bad (3) Test on hair luster

To the human head model (wig) for experiment, each hair setting foam was sprayed and the condition of the hair was visually evaluated in accordance with the following standards. The results are shown in Tables 7 and 8.

Evaluation of "hair luster"

A: Very good

B: Good

C: Fair

D: Bad (4) Test on water solubility

Each hair setting foam was coated onto a glass plate and the film thus formed was immersed in water for 5 minutes. The dissolving condition of the film was evaluated in accordance with the following standards. The results are shown in Tables 7 and 8.

"Evaluation standards of water solubility and removability upon hair washing"

A: Very good

TABLE 8

| Comparative Example | 1 | 2 | 3 | 4 |
| --- | --- | --- | --- | --- |
| Set retention | A | A | A | C |
| Stickiness | D | D | D | D |
| Stiffness | A | A | A | C |
| Water solubility | A | A | A | A |
| Luster | A | A | A | B |
| Removability | D | D | D | B |

As is understood from Table 7–8, the hair setting foams of Comparative Examples 1–4 have stickiness and besides, those of Comparative Examples 1–3 are inferior in removability with a shampoo. On the contrary, hair setting foams of Examples 1–15 satisfy both of these conditions at the same time and have excellent set retention. In particular, those containing poly(N-propionyl ethylene-imine) having a molecular weight of 5,000–10,000 tend to be superior.

What is claimed is:

1. A film-forming resin which is a copolymer comprising:

(a) 30 mol % to 80 mol % of a (meth)acrylamide monomer represented by the following formula (1):

$$CH_2=C\begin{matrix}R^1\\ \\C-N\\ \| \quad \backslash\\O \quad R^3\end{matrix}R^2 \qquad (1)$$

wherein $R^1$ represents a hydrogen atom or a methyl group, $R^2$ and $R^3$ are the same or different and each independently represents a hydrogen atom or a $C_{4-12}$ alkyl group with the proviso that $R^2$ and $R^3$ do not represent a hydrogen atom at the same time;

(b) 2 mol % to 50 mol % of a (meth)acrylamide monomer represented by the following formula (2):

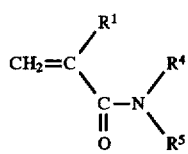 (2)

wherein $R^1$ has the same meaning as defined above, and $R^4$ and $R^5$ are the same or different and each independently represents a hydrogen atom or a $C_{1-3}$ alkyl group;

(c) 0.0001 mol % to 50 mol % of a (meth) acrylate monomer or (meth)acrylamide monomer represented by the following formula (3):

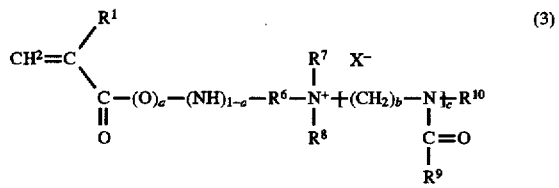 (3)

wherein $R^1$ has the same meaning as defined above, $R^6$ represents a $C_{2-3}$ alkylene group, $R^7$ and $R^8$ are the same or different and each independently represents a methyl or ethyl group, $R^9$s are the same or different and each independently represents a $C_{1-22}$ alkyl or phenyl group, $R^{10}$ represents a methyl or ethyl group, a stands for an integer of 0 or 1, b represents an integer of 2 or 3, c represents an integer of 2–10,000 and $X^-$ represents a counterion of a quaternary ammonium salt;

(d) 0 mol % to 40 mol % of a (meth)acrylate monomer represented by the following formula (4):

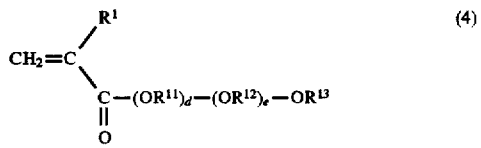 (4)

wherein $R^1$ has the same meaning as defined above, $R^{11}$ and $R^{12}$ are the same or different and each independently represents a $C_{2-4}$ alkylene group, $R^{13}$ represents a hydrogen atom, a $C_{1-10}$ alkyl group or a phenyl group, d and e each independently represents an integer of 0–50 with the proviso that they do not stand for 0 at the same time; and (e) 0 mol % to 20.0 mol % of a cross-linkable vinyl monomer.

2. A film-forming resin according to claim 1, wherein the copolymer has a molecular weight of from 10,000 to 500,000.

3. A hair cosmetic composition comprising the film-forming resin according to claim 1 or 2.

4. A hair cosmetic composition according to claim 3, which is in the form suited to set hair style.

* * * * *